United States Patent
Kelly (10) Patent No.: US 12,246,150 B2
(45) Date of Patent: *Mar. 11, 2025

(54) INFUSION BALLOON AND METHODS FOR USE THEREOF

(71) Applicant: Sanford Health, Sioux Falls, SD (US)

(72) Inventor: Patrick W. Kelly, Sioux Falls, SD (US)

(73) Assignee: Sanford Health, Sioux Falls, SD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/311,983

(22) Filed: May 4, 2023

(65) Prior Publication Data

US 2023/0347114 A1   Nov. 2, 2023

Related U.S. Application Data

(63) Continuation of application No. 16/491,861, filed as application No. PCT/US2018/021358 on Mar. 7, 2018, now Pat. No. 11,690,981.

(Continued)

(51) Int. Cl.
*A61M 25/10*   (2013.01)

(52) U.S. Cl.
CPC ... *A61M 25/1018* (2013.01); *A61M 2025/105* (2013.01); *A61M 2025/1086* (2013.01)

(58) Field of Classification Search
CPC .......... A61M 25/1018; A61M 25/1002; A61M 25/1025; A61M 25/1011;

(Continued)

(56) References Cited

U.S. PATENT DOCUMENTS 8,388,573 B1   3/2013   Cox
9,339,634 B2   5/2016   Cox
(Continued)

FOREIGN PATENT DOCUMENTS

WO   2014/165751 A1   10/2014
WO   2015/187872 A1   12/2015

OTHER PUBLICATIONS

International Search Report and Written Opinion for corresponding PCT application No. PCT/US2018/021358 dated Jun. 21, 2018.
(Continued)

*Primary Examiner* — Michael J Tsai
*Assistant Examiner* — Justin L Zamory
(74) *Attorney, Agent, or Firm* — McDonnell Boehnen Hulbert & Berghoff LLP (57) ABSTRACT

The present disclosure provides an apparatus including: (a) a frame having a first end and a second end, wherein the frame includes a plurality of struts arranged between the first end and the second end of the frame, (b) a plurality of channels disposed within the plurality of struts of the frame, (c) an infusion balloon coupled to the frame and arranged such that, in an expanded condition, the frame provides a plurality of openings that the infusion balloon is configured to expand through and extend radially outward from the frame, thereby defining a plurality of grooves, (d) a plurality of holes defined in the frame and configured to permit fluid communication between the plurality of channels and the plurality of grooves, and (e) an infusion hub arranged at the first end or the second end of the frame including a reservoir in fluid communication with the plurality of channels.

20 Claims, 9 Drawing Sheets

Related U.S. Application Data (60) Provisional application No. 62/468,330, filed on Mar. 7, 2017.

(58) Field of Classification Search
CPC .... A61M 2025/105; A61M 2025/1086; A61M 2025/1081; A61M 2025/1052
See application file for complete search history.

(56) References Cited

U.S. PATENT DOCUMENTS

| | | |
|---|---|---|
| 10,123,814 B2 | 11/2018 | Bashir |
| 2002/0077594 A1* | 6/2002 | Chien ................. A61M 25/104 604/509 |
| 2009/0270906 A1 | 10/2009 | Tossainy |
| 2012/0059401 A1* | 3/2012 | Konstantino ........... A61F 2/958 606/159 |
| 2015/0283360 A1 | 10/2015 | Kelly |

OTHER PUBLICATIONS

Thrombolex Nabs 510(k) Clearance for Catheter System, FDAnews Device Daily Bulletin dated May 17, 2019, retrieved on May 3, 2023, https://www.fdanews.com/articles/191324-thrombolex-nabs-510k-clearance-for-catheter-system.

Thrombolex—2019 Website, long version—our products, retrieved on Sep. 4, 2019, https://vimeo.com/325494722.

* cited by examiner

INFUSION BALLOON AND METHODS FOR USE THEREOF

RELATED APPLICATIONS

The present application is a continuation of U.S. patent application Ser. No. 16/491,861 entitled "Infusion Balloon and Methods for Use Thereof," filed Sep. 6, 2019, which is a U.S. National Phase application of, and claims the benefit of, International (PCT) Application No. PCT/US2018/021358 entitled "Infusion Balloon and Methods for Use Thereof," filed Mar. 7, 2018, which claims priority to U.S. Provisional Application No. 62/468,330 entitled "Infusion Balloon and Expandable Frame and Methods for Use Thereof," filed on Mar. 7, 2017, the contents of each of which are hereby incorporated by reference in their entirety

BACKGROUND THE INVENTION

Local drug delivery is the process by which therapeutic agents are delivered to specific areas within the vasculature of a human or animal patient. This localized treatment permits an increased concentration of the drug or therapeutic agent at the intended target area but avoids toxicity that may result through general systemic delivery within the circulatory system. Known localized drug delivery methods include drug-eluting stents or balloons, porous drug infusion balloons and direct catheter delivery.

SUMMARY OF THE INVENTION

The present disclosure is directed to methods and apparatus for the delivery of a drug solution or a therapeutic agent to a selected site within the vascular system using an apparatus including a frame and an infusion balloon. The apparatus may beneficially permit an increased balloon length that may be up to four times longer than that of other known balloons providing the advantage of treating larger injury sites in a single procedure. The apparatus may also provide a plurality of grooves for receiving the drug solution during delivery to the treatment site. These grooves may beneficially guide the flow of the drug solution through the treatment site, while at the same time slowing the drug flow to increase the amount of time that the drug is in contact with the wall of the treatment site. The infusion balloon and the balloon's associated channels also can help to minimize the volume of drug solution required by occupying a portion of the luminal volume. In addition, the apparatus may further include an occlusion balloon that may inflate upstream from the infusion balloon to permit adequate pressure to be maintained in the system during infusion to effectively advance the drug or therapeutic agent into and along the plurality of grooves on the outer surface of the drug delivery balloon. The occlusion balloon also helps to prevent peripheral washout by blocking blood flow from the treatment area.

Thus, in a first aspect, an apparatus is provided that includes: (a) a frame having a first end and a second end, wherein the frame includes a plurality of struts arranged between the first end and the second end of the frame, (b) a plurality of channels disposed within the plurality of struts of the frame, (c) an infusion balloon coupled to the frame and arranged such that, in an expanded condition, the frame provides a plurality of openings that the infusion balloon is configured to expand through and extend radially outward from the frame, thereby defining a plurality of grooves, (d) a plurality of holes defined in the frame, wherein the plurality of holes are configured to permit fluid communication between the plurality of channels and the plurality of grooves, and (e) an infusion hub arranged at the first end or the second end of the frame, wherein the infusion hub includes a reservoir in fluid communication with the plurality of channels.

In a second aspect, another apparatus is provided that includes: (a) a frame having a first end and a second end, wherein the frame includes a plurality of struts arranged between the first end and the second end of the frame, (b) a capillary-action material coupled to the plurality of struts of the frame, (c) an infusion balloon coupled to the frame and arranged such that, in an expanded condition, the frame provides a plurality of openings that the infusion balloon is configured to expand through and extend radially outward from the frame, thereby defining a plurality of grooves, and (d) an infusion hub arranged at the first end or the second end of the frame, wherein the infusion hub includes a reservoir and a plurality of openings to permit fluid communication with the capillary-action material.

In a third aspect, an apparatus is provided that includes: (a) a frame having a first end and a second end, wherein the frame includes a plurality of struts arranged between the first end and the second end of the frame, (b) an infusion balloon coupled to the frame and arranged such that, in an expanded condition, the frame provides a plurality of openings that the infusion balloon is configured to expand through and extend radially outward from the frame, thereby defining a plurality of grooves, (c) an occlusion balloon arranged adjacent to the first end of the frame, wherein the occlusion balloon and the infusion balloon are configured to be in fluid communication with a balloon inflation port, and (d) one or more drug delivery ducts disposed between the occlusion balloon and the infusion balloon.

In a fourth aspect, a method is provided that includes: (a) delivering the apparatus of any of the aspects described above via a catheter over a guidewire to a treatment site, (b) inflating the occlusion balloon and the infusion balloon, thereby causing the frame to expand and the infusion balloon to expand through the plurality of openings and extend radially outward thereby defining a plurality of grooves, (c) injecting a drug solution into a drug delivery lumen of the catheter in fluid communication with the infusion hub, and (d) advancing the drug solution through the drug delivery lumen to the infusion hub into the plurality of channels of the frame through the plurality of holes to the plurality of grooves and into the treatment site.

These as well as other aspects, advantages, and alternatives, will become apparent to those of ordinary skill in the art by reading the following detailed description, with reference where appropriate to the accompanying drawings.

DETAILED DESCRIPTION OF THE INVENTION

Exemplary apparatus and methods are described herein. It should be understood that the word "exemplary" is used herein to mean "serving as an example, instance, or illustration." Any embodiment or feature described herein as "exemplary" is not necessarily to be construed as preferred or advantageous over other embodiments or features. The exemplary embodiments described herein are not meant to be limiting. It will be readily understood that certain aspects of the apparatus and methods can be arranged and combined in a wide variety of different configurations, all of which are contemplated herein.

Furthermore, the particular arrangements shown in the figures should not be viewed as limiting. It should be understood that other embodiments may include more or less of each element shown in a given figure. Further, some of the illustrated elements may be combined or omitted. Yet further, an exemplary embodiment may include elements that are not illustrated in the figures.

As used herein, with respect to measurements, "about" means+/−5%.

As used herein, "coupled" means associated directly, as well as indirectly. For example, a member A may be directly associated with a member B, or may be indirectly associated therewith, e.g., via another member C. It will be understood that not all relationships among the various disclosed elements are necessarily represented.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

Reference herein to "one embodiment" or "one example" means that one or more feature, structure, or characteristic described in connection with the example is included in at least one implementation. The phrases "one embodiment" or "one example" in various places in the specification may or may not be referring to the same example.

As used herein, apparatus, element and method "configured to" perform a specified function is indeed capable of performing the specified function without any alteration, rather than merely having potential to perform the specified function after further modification. In other words, the apparatus, element, and method "configured to" perform a specified function is specifically selected, created, implemented, utilized, programmed, and/or designed for the purpose of performing the specified function. As used herein, "configured to" denotes existing characteristics of an apparatus, element, and method which enable the apparatus, element, and method to perform the specified function without further modification. For purposes of this disclosure, an apparatus, element, and method described as being "configured to" perform a particular function may additionally or alternatively be described as being "adapted to" and/or as being "operative to" perform that function.

As used herein, an "inflated diameter of the infusion balloon" refers to a diameter measured midway between the first end and the second of the frame.

As used herein, "capillary-action" material is the ability of a liquid to flow in narrow spaces without the assistance of, or even in opposition to, external forces like gravity (e.g., wicking action).

As used herein, "treatment site" refers to the blood vessel or artery in which the drug delivery balloon is deployed to effectively administer a drug solution. The treatment site may further include artificial lumens used, for example, as teaching aids.

As used herein, "drug solution" refers to any flowable material that may be administered into a treatment site. When the drug solution comprises a therapeutic to be administered to a subject, any suitable drug that can be administered in solution can be used. In various non-limiting embodiments, the therapeutic may comprise sirolimus, heparin, and cell-based therapies; and antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, (e.g., TAXOL® by Bristol-Myers Squibb Co., Stamford, Conn.), docetaxel (e.g., Taxotere®, from Aventis S. A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.).

Examples of such antiplatelets, anticoagulants, antifibrin, and antithrombins include aspirin, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet infusion balloon receptor antagonist antibody, recombinant hirudin, and thrombin inhibitors such as Angiomax a (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, proteins, peptides, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate agents include cisplatin, insulin sensitizers, receptor tyrosine kinase inhibitors, carboplatin, alpha-interferon, genetically engineered epithelial cells, steroidal anti-inflammatory agents, non-steroidal anti-inflammatory agents, antivirals, anticancer drugs, anticoagulant agents, free radical scavengers, estradiol, antibiotics, nitric oxide donors, super oxide dismutases, super oxide dismutases mimics, 4-amino-2,2,6,6-tetramethylpiperidine-1-oxyl (4-amino-TEMPO), tacrolimus, dexamethasone, ABT-578, clobetasol, cytostatic agents, prodrugs thereof, co-drugs thereof, and a combination thereof. Other therapeutic substances or agents may include rapamycin and structural derivatives or functional analogs thereof, such as 40-O-(2-hydroxy)ethyl-rapamycin (known by the trade name of EVEROLIMUS), 40-O-(3-hydroxy)propyl-rapamycin, 40-O-[2-(2-hydroxy)ethoxy]ethyl-rapamycin, methyl rapamycin, and 40-O-tetrazole-rapamycin. In addition, non-therapeutic fluids, such as water, may be used, if the apparatus is being used in a teaching model or training demonstration, for example.

In the following description, numerous specific details are set forth to provide a thorough understanding of the disclosed concepts, which may be practiced without some or all of these particulars. In other instances, details of known apparatus and/or methods have been omitted to avoid unnecessarily obscuring the disclosure. While some concepts will be described in conjunction with specific examples, it will be understood that these examples are not intended to be limiting.

Figure 1:
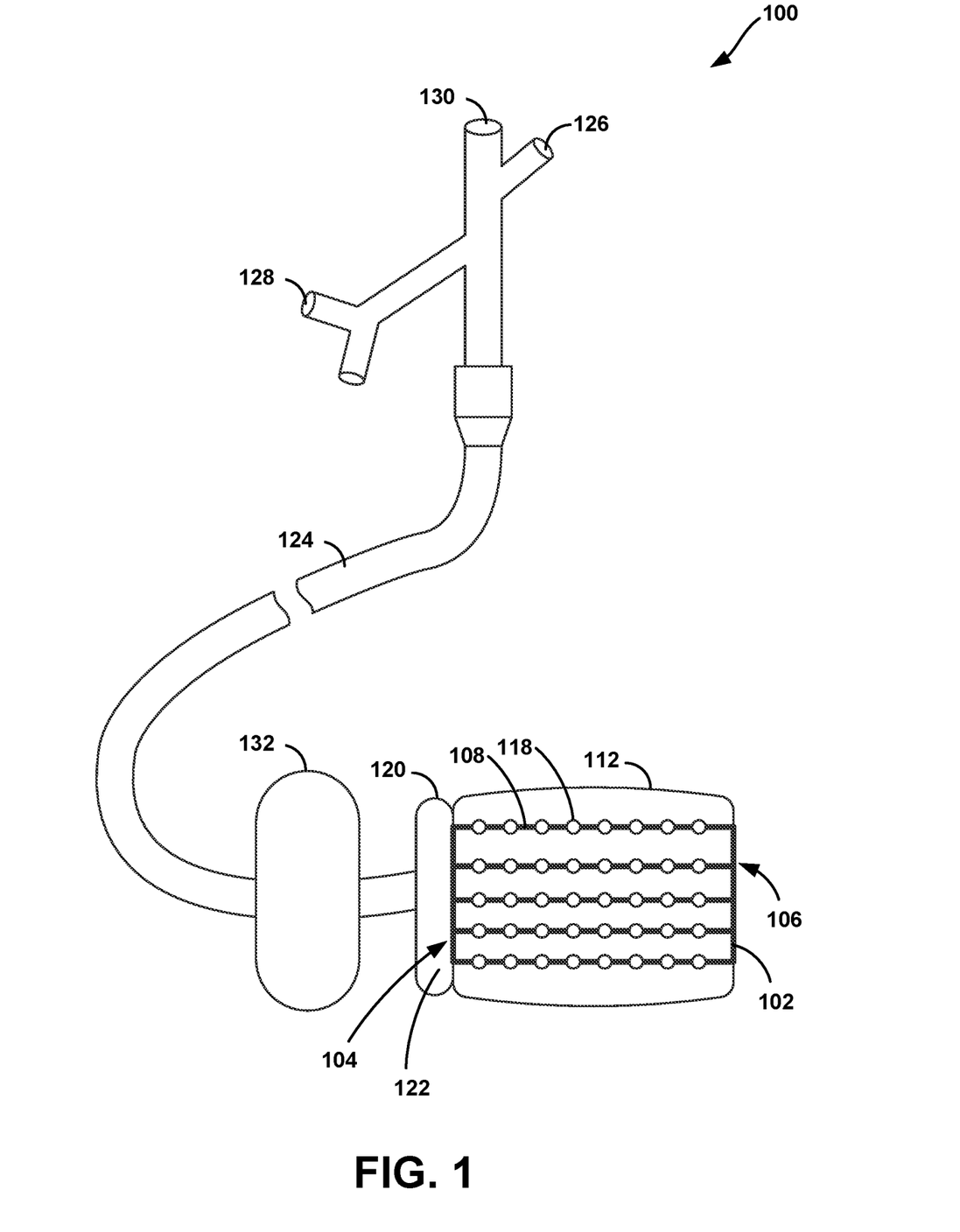
FIG. 1 is a top view of an apparatus, according to an example embodiment.

With respect to the figures, FIG. 1 illustrates a top view of an apparatus 100, according to an example embodiment. The apparatus 100 includes a frame 102 having a first end 104 and a second end 106. The frame 102 may range in length from about 50 mm to about 200 mm. In various embodiments, the length of the frame 102 ranges from about 80 mm to about 200 mm, from about 100 mm to about 200 mm, from about 120 mm to about 200 mm, from about 140 mm to about 200 mm, from about 160 mm to about 200 mm, from about 180 mm to about 200 mm, from about 60 mm to about 120 mm, from about 60 mm to about 100 mm, and from about 10 mm to about 80 mm.

The frame 102 includes a plurality of struts 108 arranged between the first end 104 and the second end 106 of the frame 102. The frame 102 and corresponding struts 108 may be made of nitinol or various biocompatible polymers. In optional embodiments, the plurality of struts 108 have an arrangement that is at least helical, longitudinal, sinusoidal, cross-hatched, or latticed, as non-limiting examples. In one example, the frame 102 comprises two to eight struts 108. The plurality of struts 108 may be substantially straight from the first end 104 of the frame 102 to the second end 106 of the frame 102, or the plurality of struts 108 may be curved from the first end 104 of the frame 102 to the second end 106 of the frame 102. Such a curve may be helical, longitudinal, sinusoidal, for example. In one example, the plurality of struts 108 comprises at least one strut arranged longitudinally and at least one strut arranged circumferentially. In such an example, the at least one strut arranged circumferentially may be cross-hatched, or latticed, as non-limiting examples. The apparatus 100 also includes a plurality of channels 110 disposed within the plurality of struts 108 of the frame 102. In one example, the plurality of channels 110 form an interconnected network within the plurality of struts 108, as illustrated in the front cross-sectional view of the apparatus 100 in FIG. 2. In one example, the plurality of struts 108 are hollow thereby defining the plurality of channels 110.

Figure 2:
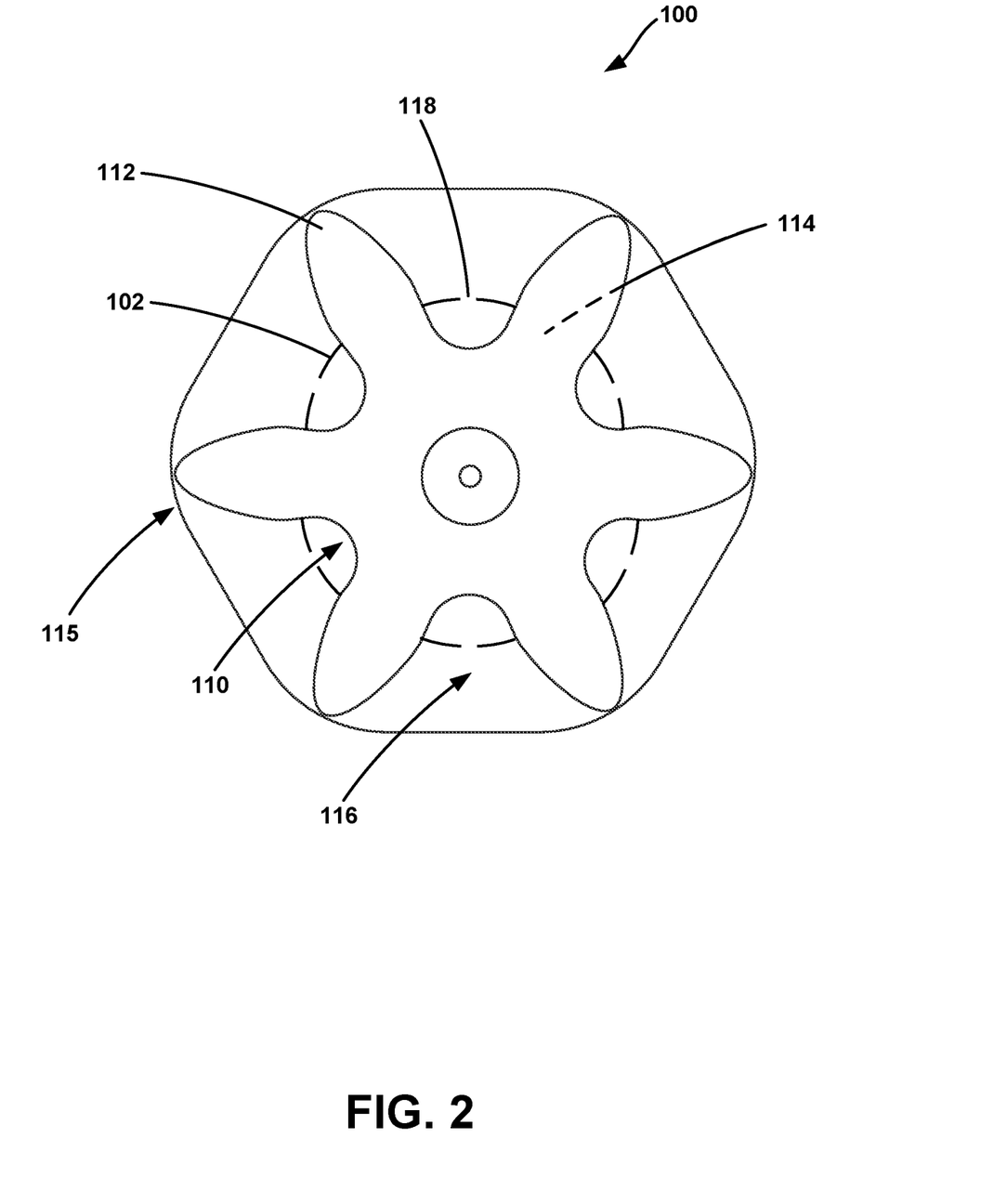
FIG. 2 is a front cross-sectional view of the apparatus of FIG. 1, according to an example embodiment.

The apparatus 100 also includes an infusion balloon 112 coupled to the frame 102. In various examples, the infusion balloon 112 may be either coupled to an interior of the frame 102, coupled to an exterior of the frame 102, or embedded within the frame 102. The infusion balloon 112 may be made of compliant materials such as polyurethane, latex, or silicone that results in a low burst pressure of about 5 atm, for example. The infusion balloon 112 may be configured to transition from a compressed condition (i.e., during delivery of the apparatus 100 to a treatment site) to an expanded condition. The infusion balloon 112 may be arranged such that, in the expanded condition, the frame 102 provides a plurality of openings 114 that the infusion balloon 112 is configured to expand through and extend radially outward from the frame 102, thereby defining a plurality of grooves 116. The plurality of grooves 116 are defined by the space between adjacent portions of the infusion balloon 112 that expend through and extend radially outward from adjacent openings 114 in the frame 102, as shown in FIG. 2.

Figure 4:
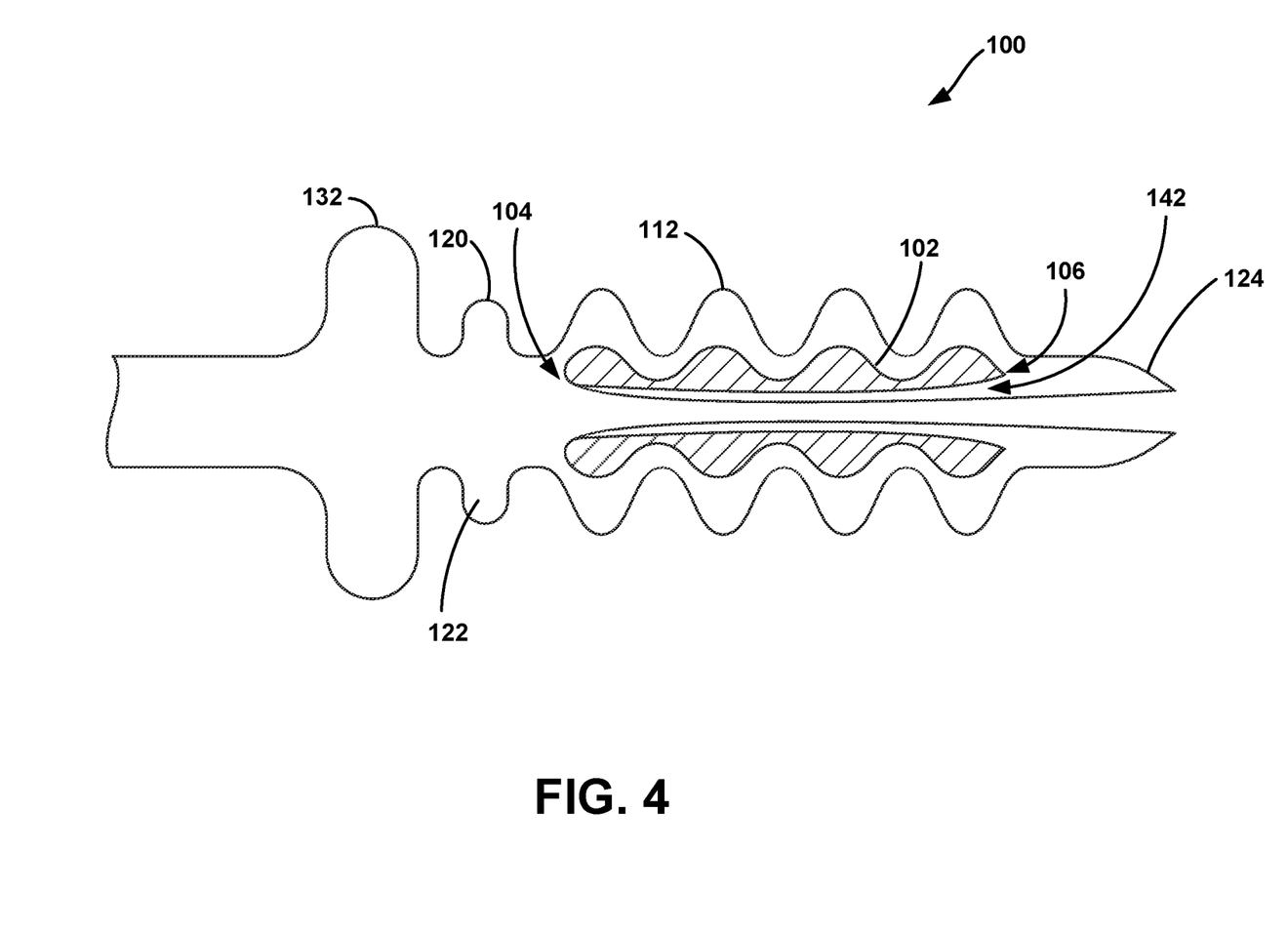
FIG. 4 is a side cross-sectional view the apparatus of FIG. 1 with a helical, longitudinal, sinusoidal, cross-hatched, or latticed infusion balloon, according to an example embodiment.

The plurality of grooves 116 may serve to (1) guide the flow of a drug solution and (2) slow the flow of the drug solution to increase the time of contact of the drug with the vessel wall 115 of the treatment site. The plurality of grooves 116 are preferably axially aligned with a central axis of the infusion balloon 112 and may be spiraled, helical, sinusoidal or substantially straight, among other possibilities, in various embodiments. In one particular example, as shown in FIG. 4, the infusion balloon 112 itself may include helical, longitudinal, sinusoidal, cross-hatched, or latticed sections. In another example, as discussed above, the plurality of struts 108 of the frame are helical, longitudinal, sinusoidal, cross-hatched, or latticed. Spiraled, helical or sinusoidal grooves may be preferred over straight grooves, because the more tortuous grooves provide more surface area to contact the target vessel wall 115 and further extend the amount of time that the drug solution contacts the target vessel wall 115. Further, any pattern of grooves is contemplated including a cross-hatched or waffle pattern, for example. The shape of the plurality of grooves 116 may mirror the shape of the plurality of openings 114 in the frame 102.

In one example, the frame 102 includes the plurality of openings 114 when the infusion balloon 112 is in both the compressed condition and the expanded condition. In another example, the plurality of openings 114 in the frame 102 are only present when the infusion balloon 112 is in the expanded condition. In such an example, the frame 102 may have a higher Young's modulus than that of the infusion balloon 112 such that the frame 102 and infusion balloon 112 expand at different rates in response to the same pressure.

The apparatus 100 also includes a plurality of holes 118 defined in the frame 102. The plurality of holes 118 are configured to permit fluid communication between the plurality of channels 110 and the plurality of grooves 116. In one example, the plurality of holes 118 are open when the infusion balloon 112 is in both the compressed condition and the expanded condition. In another example, the plurality of holes 118 are closed when the infusion balloon 112 is in the compressed condition, and the plurality of holes 118 are open when the infusion balloon 112 is in the expanded condition. In such an example, each of the plurality of holes 118 may include valves that open in response to the pressure applied by the infusion balloon 112 as the infusion balloon 112 inflates. The apparatus 100 also includes an infusion hub 120 arranged at the first end 104 or the second end 106 of the frame 102. The infusion hub 120 includes a reservoir 122 in fluid communication with the plurality of channels 110. The reservoir 122 of the infusion hub 120 may be configured to receive a drug solution to more evenly distribute the drug solution through the plurality of channels 110, out of the plurality of holes 118, and into the plurality of grooves 116. The reservoir 122 of the infusion hub 120 may be circumferential.

Figure 3:
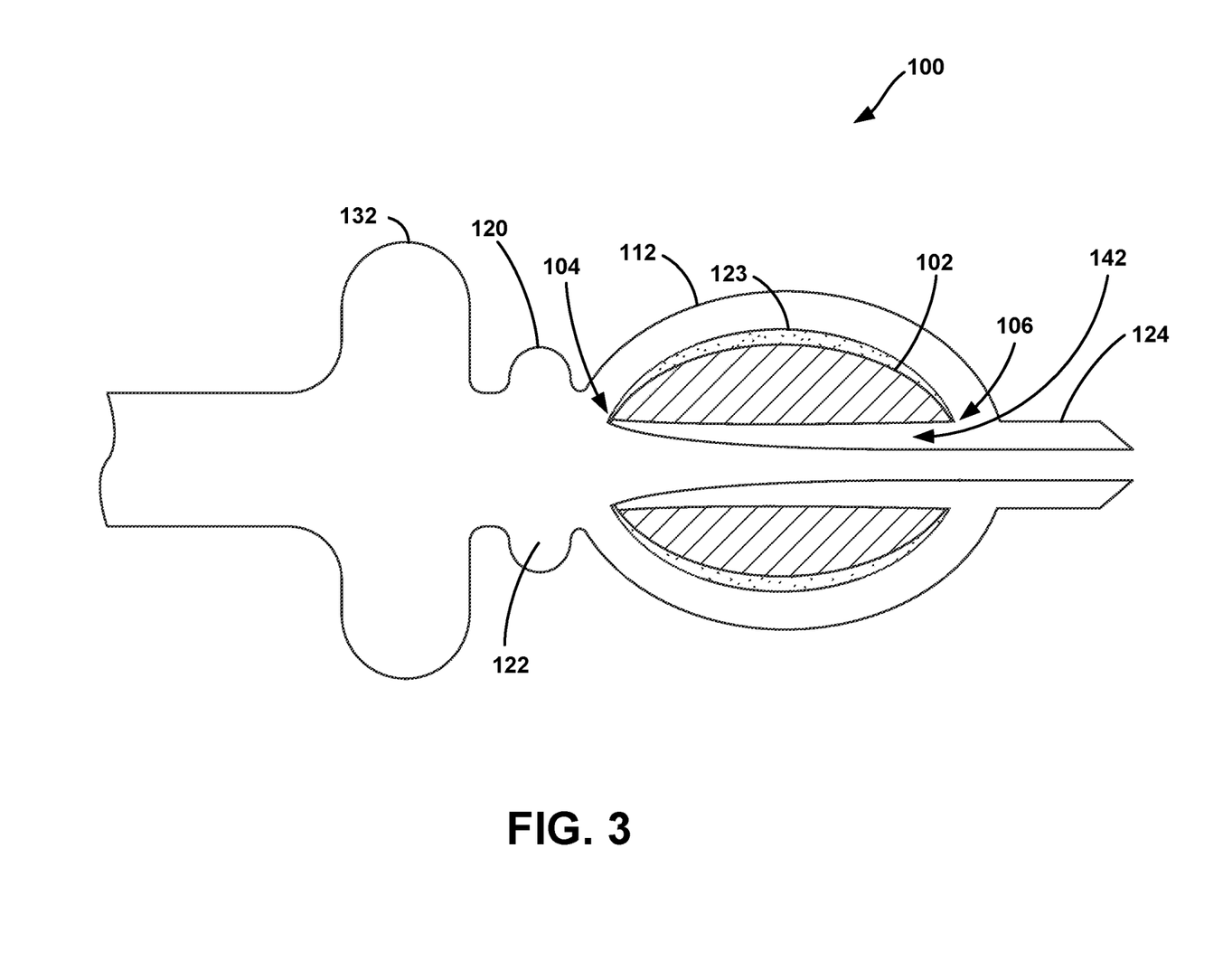
FIG. 3 is a side cross-sectional view of the apparatus of FIG. 1, according to an example embodiment.

In one embodiment, the apparatus 100 also includes a capillary-action material 123 coupled to the struts 108 of the frame 102, as shown in FIG. 3. Example materials for the capillary-action material 123 may include biological, biosynthetic and synthetic microtubules, thin tubes, or porous materials. Capillary-action may result from intermolecular forces between a liquid and surrounding solid surfaces. For example, a diameter of a thin tube is sufficiently small, then the combination of surface tension, caused by cohesion within the liquid, and adhesive forces between the liquid and tubular wall act to propel the liquid along the length of the tube. In operation, the capillary-action material 123 is configured to transport a fluid along the plurality of struts 108 of the frame 102 thereby placing the fluid in contact with a treatment site. In various embodiments, the capillary-action material 123 is configured to expand with the frame 102. In some embodiments, the microtubules and thin tubes may be arranged with their first ends adjacent to the infusion hub 120 and their second ends arranged in a staggered configuration along the length of the plurality of struts 108 to evenly distribute the fluid along the length of the plurality of grooves 116.

In one embodiment, the apparatus 100 also includes a catheter 124 having at least one lumen. In such an example, the apparatus 100 may also include a balloon inflation port 126 in communication with the at least one lumen, a drug delivery port 128 in communication with the at least one lumen through which a drug solution is administered, and a guidewire port 130 in communication with the at least one lumen for receiving a guidewire. The apparatus 100 may also include an occlusion balloon 132 arranged adjacent to the first end 104 of the frame 102. The occlusion balloon 132 and the infusion balloon 112 are configured to be in fluid communication with the balloon inflation port 126 such that the balloon inflation port 126 is used to inflate both the occlusion balloon 132 and the infusion balloon 112. In one example embodiment, the drug delivery port 128 may be bifurcated, as shown in FIG. 1, such that two, three, four or more different drug solutions or other solutions may be introduced into the drug delivery port 108 as deemed appropriate for treatment.

The occlusion balloon 132 may be composed of atraumatic compliant materials such as polyurethane, latex, or silicone, among other possibilities, that results in a low burst pressure of about 5 atm, for example. However, the occlusion balloon 132 may be configured to withstand greater pressures, for example up to about 20 atm. The occlusion balloon 132 may be configured to conform to the shape and size of the treatment site via low pressure inflation, about 1 to 2 atm. Once inflated, the occlusion balloon 132 may provide occlusion in the treatment site to allow for drug delivery into the treatment site downstream from the occlusion balloon 132 to minimize dilution of the drug solution from blood flow. The inflated diameter of both the infusion balloon 112 and the occlusion balloon 132 may range from about 2.5 mm to about 24 mm. The length of the occlusion balloon 132 may range from about 20 mm to about 40 mm. In one embodiment, the inflated diameter of the occlusion balloon 132 ranges from about the same as the inflated diameter of the infusion balloon 112 to about 2 mm to about 6 mm larger than the inflated diameter of the infusion balloon 112. The occlusion balloon 132 and the frame 102 may be separated from each other by a distance ranging from about 2 mm to about 20 mm. This distance allows adequate pressure to be maintained in the system such that the drug solution may be effectively advanced into and along the plurality of grooves 116. In operation, the occlusion balloon 132 may be inflated prior to the introduction of the drug solution into the infusion hub 120.

Figure 5:
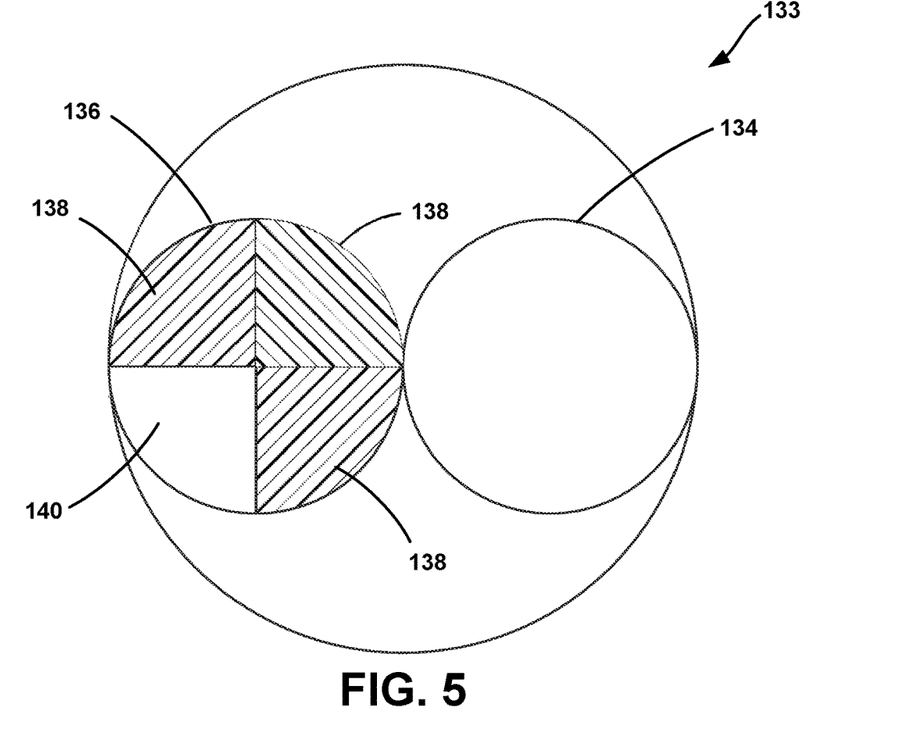
FIG. 5 is a front cross-sectional view of a two lumen configuration of the apparatus, according to an example embodiment.

In one example, the at least one lumen of the catheter 124 comprises two parallel lumens 133. FIG. 5 illustrates a front cross-sectional view of the two lumens 133. In particular, the apparatus 100 may include an infusion lumen 134 in communication with the balloon inflation port 126 and may be configured to receive a saline contrast mixture, or any other suitable fluid medium, to inflate the occlusion balloon 132 and the infusion balloon 112. Further, the apparatus 100 may include a guidewire lumen 136 in communication with the drug delivery port 128 and the guidewire port 130. In one embodiment, the second lumen 116 may be sized and shaped to receive a drug solution. In one embodiment, the second lumen 116 may also be sized and shaped to receive a guidewire having a diameter in the range from about 0.25 mm to about 1 mm, and preferably in a range from about 0.254 mm to about 0.9652 mm. The guidewire lumen 136 may include one or more drug delivery channels 138 extending the length of the guidewire lumen 136. These drug delivery channels 138 may be used to transport the drug solution from the drug delivery port 128 to a treatment site. The guidewire lumen 136 may also include a guidewire channel 140 extending the length of the guidewire lumen 136. In another example, the guidewire lumen 136 may include a single channel for both the guidewire and drug solution.

In such a configuration, the guidewire may be removed after use so that the drug solution can pass through the guidewire lumen 136. In operation, the apparatus 100 may be configured to infuse the drug solution while the guidewire is in the guidewire lumen 136. In such a configuration, the guidewire lumen 136 may have a larger diameter than the guidewire from a location between the guidewire port 130 and the drug delivery port 128 until just distal to the infusion hub 120. The guidewire lumen 136 would shrink down to about the diameter of the guidewire just distal to the infusion hub 120 to the distal end of the frame 102. Further, the guidewire lumen 136 would shrink down to about the diameter of the guidewire proximal to the infusion hub 120, so as to prevent the drug solution from exiting the guidewire port 130. In another example, a flange or one-way valve may be used to prevent the drug solution from exiting the guidewire port 130. In yet another example, a portion of the catheter 124 surrounded by the frame 102 has a chamber 142 in fluid communication with the infusion port 120. In such an example, when the infusion balloon 112 is in the expanded condition, the chamber 142 configured to inflate radially inward within the at least one lumen to thereby form a seal with a guidewire distal to the infusion hub 120. Other configurations are possible as well.

Figure 6:
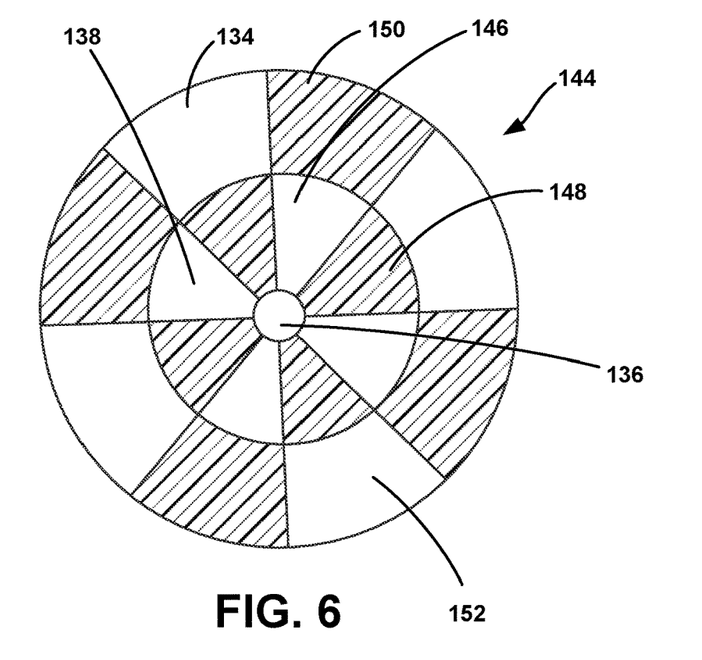
FIG. 6 is a front cross-sectional view of a three lumen configuration of the apparatus, according to an example embodiment.

In another embodiment, the balloon inflation port 126, the drug delivery port 128, and the guidewire port 130 may be coupled to three concentrically aligned lumens 144. For example, FIG. 6 illustrates a front cross-sectional view of the three lumens 144. As shown in FIG. 6, the three concentrically aligned lumens 144 comprise a guidewire lumen 136, a drug delivery lumen 146, and an infusion lumen 134. The guidewire lumen 136 may be in communication with the guidewire port 130 and may be sized and shaped to receive a guidewire having a diameter in the range from about 0.25 mm to about 1 mm, and preferably in a range from about 0.254 mm to about 0.9652 mm. The drug delivery lumen 146 may be in communication with the drug delivery port 128. The drug delivery lumen 146 may include a plurality of flexible spacers 148 that extend between the guidewire lumen 136 and the infusion lumen 134 to maintain the structural integrity of the drug delivery lumen 146. These spacers 148, in combination with the drug delivery lumen 146 and the guidewire lumen 136, may further define one or more drug delivery channels 138 extending the length of the drug delivery lumen 146. As discussed above, these drug delivery channels 134 may be used to transport the drug solution from the drug delivery port 128 to a treatment site. The infusion lumen 134 may be in communication with the balloon inflation port 126. The infusion lumen 134 may also include a plurality of flexible spacers 150 to help maintain the structural integrity of the infusion lumen 134. These spacers 150, in combination with the infusion lumen 134 and drug delivery lumen 146, may also define a plurality of fluid delivery channels 152 extending the length of the infusion lumen 134. These fluid delivery channels 152 may be in fluid communication with the occlusion balloon 132, the infusion balloon 112, and the reservoir 122 of the infusion hub 120.

In use, the apparatus 100 of any one of embodiments described above is delivered via a catheter over a guidewire to a treatment site. Once positioned in the treatment site, the occlusion balloon 132 is inflated to provide occlusion in the treatment site to allow for drug delivery into the treatment site downstream from the occlusion balloon 132 to minimize dilution of the drug solution from blood flow. The infusion balloon 112 is then inflated, such that the frame 102 provides a plurality of openings 114 that the infusion balloon 112 is configured to expand through and extend radially outward from the frame 102, thereby defining a plurality of grooves 116. A drug solution is then provided to the drug delivery port 126 and into the reservoir 122 of the infusion hub 120. From there, the drug solution transitions through the plurality of channels 110, out of the plurality of holes 118, and into the plurality of grooves 116 and contacts the vessel wall 115 at the treatment site. The drug solution advances downstream into and along the plurality of grooves 116 defined in the outer surface of the infusion balloon 112. Once the drug solution exits the plurality of grooves 116 at the second end 106 of the frame 102, the drug solution may be cleared via normal arterial blood flow and ultimate physiological function.

Figure 7:
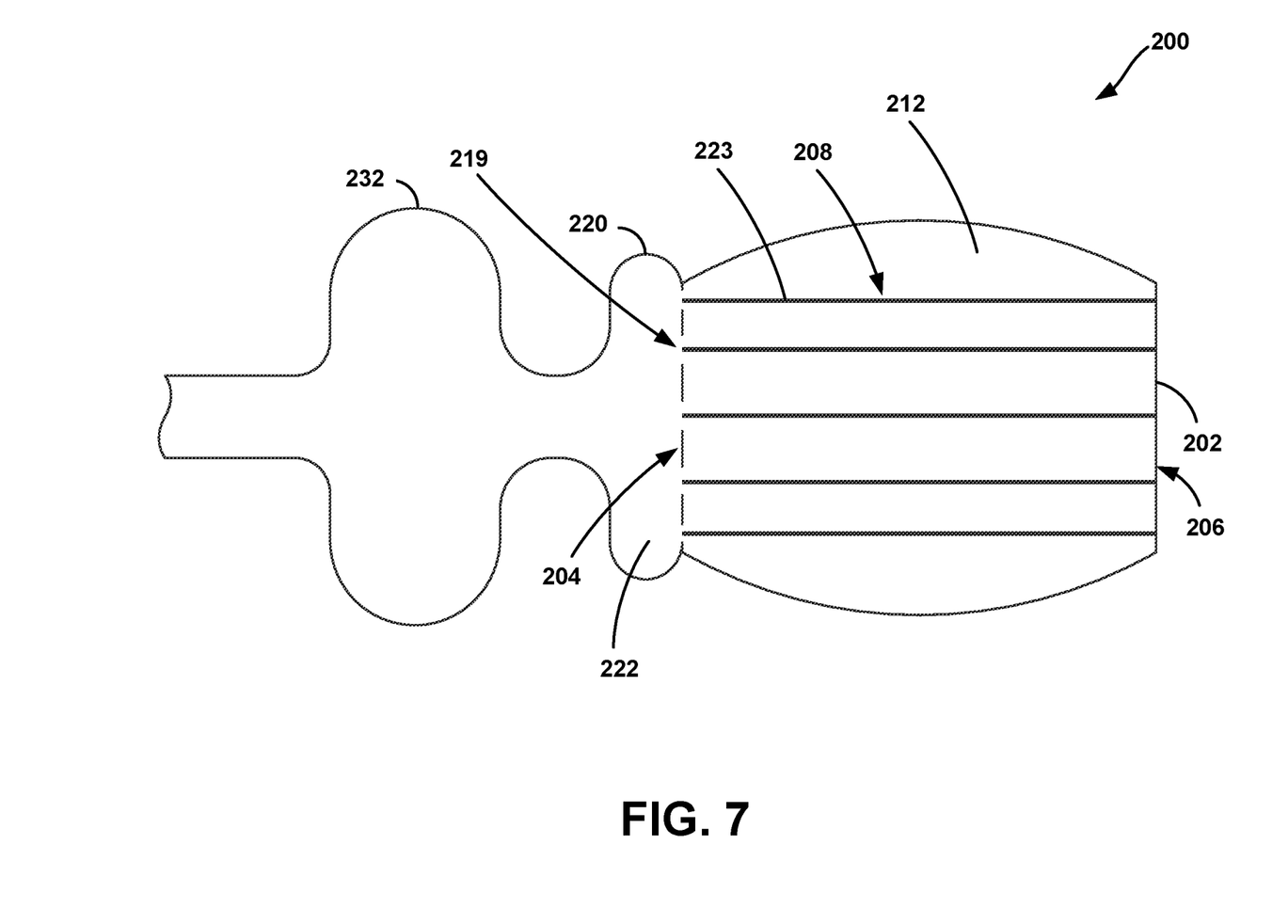
FIG. 7 is a side cross-sectional view of another apparatus, according to an example embodiment.
Figure 8:
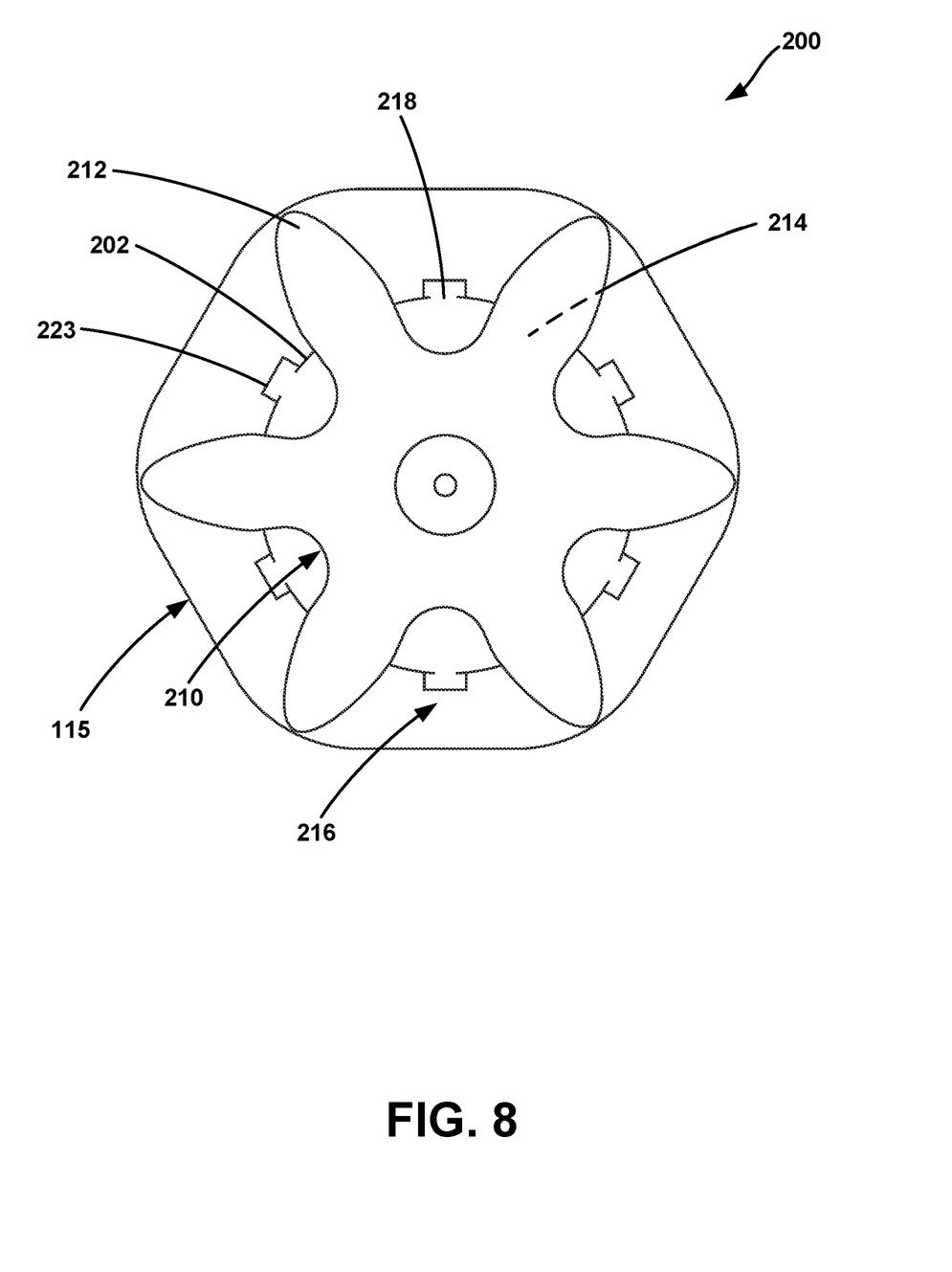
FIG. 8 is a front cross-sectional view of the apparatus of FIG. 7, according to an example embodiment.

FIG. 7 illustrates another example apparatus 200, according to an example embodiment. The apparatus 200 may include one or more features of the apparatus 100 described above. As shown in FIG. 7, the apparatus 200 includes a frame 202 having a first end 204 and a second end 206. The frame 202 includes a plurality of struts 208 arranged between the first end 204 and the second end 206 of the frame 202. The apparatus 200 also includes a capillary-action material 223 coupled to the plurality of struts 208 of the frame 202. The apparatus 200 also includes an infusion balloon 212 coupled to the frame 202. The infusion balloon 212 may be configured to transition from a compressed condition (i.e., during delivery of the apparatus 200 to a treatment site) to an expanded condition. The infusion balloon 212 may be arranged such that, in the expanded condition, the frame 202 provides a plurality of openings 214 that the infusion balloon 212 is configured to expand through and extend radially outward from the frame 202, thereby defining a plurality of grooves 216. The plurality of grooves 116 are defined by the space between adjacent portions of the infusion balloon 112 that expend through and extend radially outward from adjacent openings 114 in the frame 102, as shown in FIG. 8. The apparatus 200 also includes an infusion hub 220 arranged at the first end 204 or the second end 206 of the frame 202. The infusion hub 220 includes a reservoir 222 and a plurality of openings 219 to permit fluid communication with the capillary-action material.

As discussed above, example materials for the capillary-action material 223 may include biological, bio-synthetic and synthetic microtubules, thin tubes, or porous materials. Capillary-action may result from intermolecular forces between a liquid and surrounding solid surfaces. For example, a diameter of a thin tube is sufficiently small, then the combination of surface tension, caused by cohesion within the liquid, and adhesive forces between the liquid and tubular wall act to propel the liquid along the length of the tube. In operation, the capillary-action material 223 is configured to transport a fluid along the plurality of struts 208 of the frame 202 thereby placing the fluid in contact with a treatment site. In various embodiments, the capillary-action material 223 is configured to expand with the frame 202. In some embodiments, the microtubules and thin tubes may be arranged with their first ends adjacent to the infusion hub 220 and their second ends arranged in a staggered configuration along the length of the plurality of struts 208 to evenly distribute the fluid along the length of the plurality of grooves 216.

In one embodiment, the apparatus 200 further includes a plurality of channels 210 disposed within the plurality of struts 208 of the frame 202. In such an example, the apparatus 200 further includes a plurality of holes 218 defined in the plurality of struts 208, as shown in FIG. 8. The plurality of holes 218 are configured to permit fluid communication between the plurality of channels 210 and the capillary-action material 223.

Figure 9:
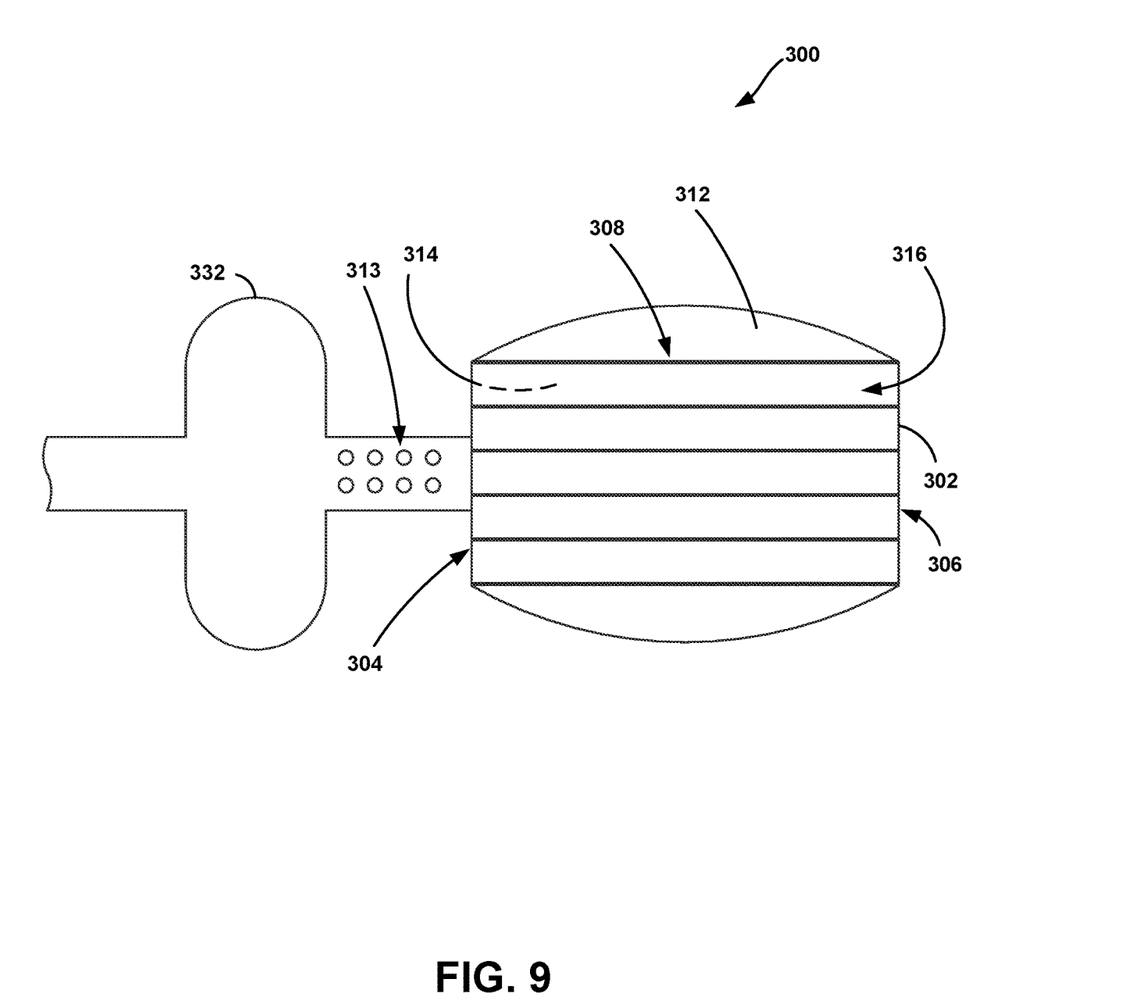
FIG. 9 is a top view of yet another apparatus, according to an example embodiment.

FIG. 9 illustrates yet another example apparatus 300, according to an example embodiment. The apparatus 300 may include one or more features of the apparatus 100 and/or the apparatus 200 described above. As shown in FIG. 9, the apparatus 300 includes a frame 302 having a first end 304 and a second end 306. The frame 302 includes a plurality of struts 308 arranged between the first end 304 and the second end 306 of the frame 302. The apparatus 300 further includes an infusion balloon 312 coupled to the frame 302. The infusion balloon 312 may be configured to transition from a compressed condition (i.e., during delivery of the apparatus 300 to a treatment site) to an expanded condition. The infusion balloon 312 may be arranged such that, in the expanded condition, the frame 302 provides a plurality of openings 314 that the infusion balloon 312 is configured to expand through and extend radially outward from the frame 302, thereby defining a plurality of grooves 316. The apparatus 300 further includes an occlusion balloon 332 arranged adjacent to the first end 304 of the frame 302. The occlusion balloon 332 and the infusion balloon 312 are configured to be in fluid communication with a balloon inflation port. The apparatus 300 further includes one or more drug delivery ducts 313 disposed between the occlusion balloon 332 and the infusion balloon 312. In other words, these drug delivery ducts 313 may be downstream from the occlusion balloon 132 in operation. The number of drug delivery ducts 313 may depend upon the distance between the occlusion balloon 132 and the infusion balloon 312 and/or the diameter of the drug delivery ducts 313, among other possibilities. In one particular example, there are between 2 and 24 drug delivery ducts 313.

Figure 10:
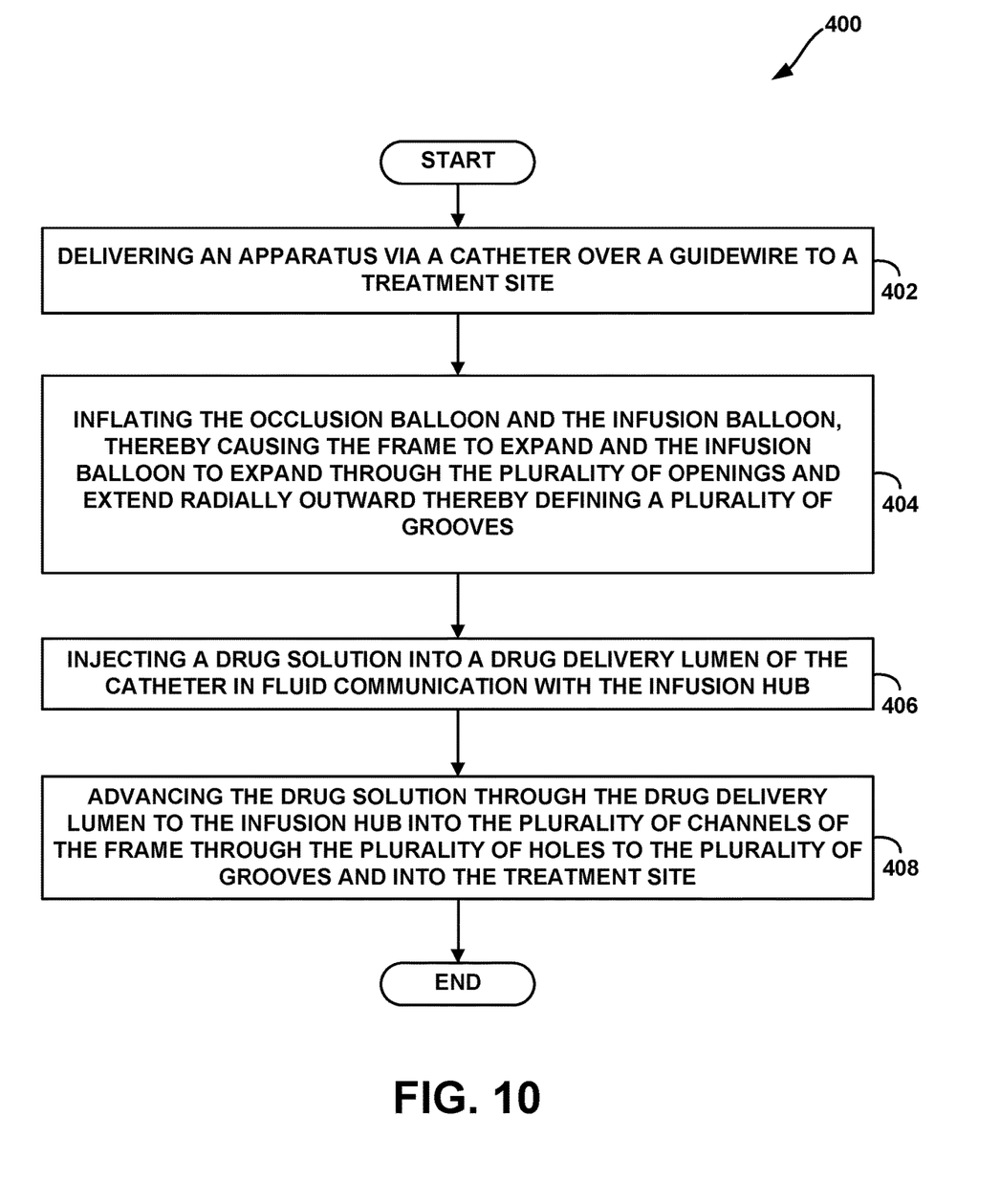
FIG. 10 is a flow chart depicting functions that can be carried out in accordance with example embodiments of the disclosed methods.

FIG. 10 is a simplified flow chart illustrating a method 400 according to an exemplary embodiment. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

At block 402, the method 400 involves delivering the apparatus of any one of embodiments described above via a catheter over a guidewire to a treatment site. The drug delivery balloon apparatus may be introduced and delivered in a standard coaxial manner, via over-the-wire or rapid exchange techniques, as examples.

At block 404, the method 400 involves inflating the occlusion balloon and the drug delivery balloon, thereby causing the frame to expand and the infusion balloon to expand through the plurality of openings and extend radially outward thereby defining a plurality of grooves. In one embodiment, the occlusion balloon and the drug delivery balloon may be inflated by injecting a saline contrast mixture, for example, into a balloon inflation port. The saline contrast mixture may then be advanced through an infusion lumen of the catheter to the occlusion balloon and the drug delivery balloon until both balloons are inflated. The occlusion balloon may inflate at a slightly faster rate, since the occlusion balloon and the drug delivery balloon are connected in series such that the occlusion balloon receives the saline contrast inflation mixture first. In another embodiment, the occlusion balloon and drug delivery balloon may be inflated using any other suitable fluid medium.

After both the occlusion balloon and the drug delivery balloon have been inflated, the method 400 continues at block 406 with injecting a drug solution into a drug delivery lumen of the catheter in fluid communication with the infusion hub. In one embodiment, the drug delivery lumen is in fluid communication with a drug delivery port of the catheter. In one particular example, the drug delivery port is bifurcated, such that two, three, four or more different drug solutions or other solutions may be introduced into the drug delivery port as deemed appropriate.

At block 408, the method 400 involves advancing the drug solution through the drug delivery lumen to the infusion hub into the plurality of channels of the frame through the plurality of holes to the plurality of grooves and into the treatment site. At this stage, the space between the occlusion balloon and the drug delivery balloon acts as a reservoir storing the drug solution as the drug solution is delivered via the drug delivery ducts. Due to the pressure at which the drug solution is being introduced to the drug delivery lumen, the drug solution advances downstream into and along the plurality of grooves defined in the outer surface of the infusion balloon. The injection of the drug solution is performed at a fluid pressure at or below about 1 atm to about 4 atm. Once the drug solution exits the plurality of grooves at the second end of the frame, the drug solution may be cleared via normal arterial blood flow and ultimate physiological function. In one example, the inflated diameter of the occlusion balloon ranges from about the same as the inflated diameter of the infusion balloon to about 2 mm to about 6 mm larger than the inflated diameter of the infusion balloon.

In one example, a common lumen is used for the drug delivery lumen and the guidewire lumen, and a portion of the catheter surrounded by the frame has a chamber in fluid communication with the infusion port. In such an example, the method 200 may further include inflating the chamber of the catheter to thereby expand a portion of an interior wall of the catheter to form a seal with the guidewire distal to the infusion hub.

While various aspects and embodiments have been disclosed herein, other aspects and embodiments will be apparent to those skilled in the art. All embodiments within and between different aspects of the invention can be combined unless the context clearly dictates otherwise. The various aspects and embodiments disclosed herein are for purposes of illustration and are not intended to be limiting, with the true scope and spirit being indicated by the claims.

The invention claimed is:

1. An apparatus, comprising:
a frame having a first end and a second end, wherein the frame includes a plurality of struts arranged between the first end and the second end of the frame;
a balloon positioned at least partially within the frame and arranged such that, in an expanded condition, the frame provides a plurality of openings that the balloon is configured to expand through and extend radially outward from the frame, thereby defining a plurality of grooves;
an occlusion balloon arranged adjacent to the first end of the frame, wherein the occlusion balloon and the balloon are configured to be in fluid communication with a balloon inflation port; and
one or more drug delivery ducts disposed between the occlusion balloon and the balloon.

2. The apparatus of claim 1, further comprising:
a catheter having at least one lumen, wherein the balloon inflation port is in communication with the at least one lumen;
a drug delivery port in communication with the at least one lumen; and
a guidewire port in communication with the at least one lumen.

3. The apparatus of claim 2, wherein the guidewire port is sized to receive a guidewire having a diameter in a range of about 0.254 mm to about 0.9652 mm.

4. The apparatus of claim 2, wherein the catheter has a chamber in fluid communication with the balloon inflation port, and wherein, in the expanded condition, the chamber is configured to inflate radially inward within the at least one lumen to thereby form a seal with a guidewire.

5. The apparatus of claim 2, wherein the at least one lumen of the catheter comprises a guidewire lumen and an infusion lumen.

6. The apparatus of claim 5, wherein the drug delivery port and the guidewire port are both in communication with the guidewire lumen of the catheter.

7. The apparatus of claim 2, wherein the at least one lumen of the catheter comprises a guidewire lumen, a drug delivery lumen, and an infusion lumen.

8. The apparatus of claim 7, wherein the drug delivery port is in communication with the drug delivery lumen and the guidewire port is in communication with the guidewire lumen of the catheter.

9. The apparatus of claim 1, wherein the occlusion balloon and the frame are separated from each other by a distance ranging from about 2 mm to about 20 mm.

10. The apparatus of claim 1, wherein the occlusion balloon and the balloon each have an inflated diameter in a range from about 2.5 mm to about 24 mm.

11. The apparatus of claim 1, wherein an inflated diameter of the occlusion balloon ranges from about the same as an inflated diameter of the balloon to about 2 mm to about 6 mm larger than the inflated diameter of the balloon.

12. The apparatus of claim 1, wherein the occlusion balloon ranges in length from about 20 mm to about 40 mm.

13. The apparatus of claim 1, wherein a number of the one or more drug delivery ducts ranges from 2 to 24.

14. The apparatus of claim 1, wherein the frame comprises two to eight struts.

15. The apparatus of claim 1, wherein the frame ranges in length from about 50 mm to about 200 mm.

16. A method, comprising:
   delivering the apparatus of claim 1 via a catheter over a guidewire to a treatment site;
   inflating the occlusion balloon and the balloon, thereby causing the frame to expand and the balloon to expand through the plurality of openings and extend radially outward thereby defining a plurality of grooves;
   injecting a drug solution into a drug delivery lumen of the catheter in fluid communication with the one or more drug delivery ducts; and
   advancing the drug solution through the drug delivery lumen to the one or more drug delivery ducts into the plurality of channels of the frame to the plurality of grooves and into the treatment site.

17. The method of claim 16, wherein injecting the drug solution is performed at a fluid pressure at or below about 1 atm to about 4 atm.

18. The method of claim 16, wherein an inflated diameter of the occlusion balloon ranges from about the same as an inflated diameter of the balloon to about 2 mm to about 6 mm larger than the inflated diameter of the balloon.

19. The method of claim 16, wherein inflating the occlusion balloon and the balloon comprises:
   injecting a saline contrast mixture into the balloon inflation port; and
   advancing the saline contrast mixture through an infusion lumen of the catheter to the occlusion balloon and the balloon.

20. The method of claim 19, wherein a common lumen is used for the drug delivery lumen and a guidewire lumen, and a portion of the catheter surrounded by the frame has a chamber in fluid communication with the balloon inflation port, the method further comprising:
   inflating the chamber of the catheter to thereby expand a portion of an interior wall of the catheter to form a seal with the guidewire.

\* \* \* \* \*